(12) United States Patent
Lang et al.

(10) Patent No.: US 7,744,784 B2
(45) Date of Patent: Jun. 29, 2010

(54) METHOD FOR PREPARING DIORGANOMAGNESIUM-CONTAINING SYNTHESIS MEANS

(75) Inventors: Sebastian Lang, Frankfurt am Main (DE); Alexander Murso, Frankfurt am Main (DE); Ulrich Wietelmann, Friedrichsdorf (DE); Uwe Lischka, Frankfurt am Main (DE); Jens Röder, Frankfurt am Main (DE)

(73) Assignee: Chemetall GmbH, Frankfurt am Main (DE)

( * ) Notice: Subject to any disclaimer, the term of this patent is extended or adjusted under 35 U.S.C. 154(b) by 0 days.

(21) Appl. No.: 12/088,110

(22) PCT Filed: Oct. 16, 2006

(86) PCT No.: PCT/EP2006/067464

§ 371 (c)(1),
(2), (4) Date: May 12, 2008

(87) PCT Pub. No.: WO2007/042578

PCT Pub. Date: Apr. 19, 2007

(65) Prior Publication Data

US 2008/0258319 A1    Oct. 23, 2008

(30) Foreign Application Priority Data

Oct. 14, 2005   (DE) .................... 10 2005 049 635
May 24, 2006   (DE) .................... 10 2006 024 915

(51) Int. Cl.
*C07F 3/02*   (2006.01)
(52) U.S. Cl. .................................. 260/665 R
(58) Field of Classification Search .............. 260/665 R
See application file for complete search history.

(56) References Cited

U.S. PATENT DOCUMENTS

| | | | | | |
|---|---|---|---|---|---|
| 2,985,692 | A | * | 5/1961 | Podall | 260/665 R |
| 2,987,558 | A | * | 6/1961 | Blitzer et al. | 260/665 R |
| 4,342,708 | A | * | 8/1982 | Sakurai et al. | 260/665 R |
| 4,455,387 | A | * | 6/1984 | McKinnie et al. | 502/153 |
| 4,976,886 | A | | 12/1990 | Morrison et al. | |
| 5,171,467 | A | * | 12/1992 | Mehta et al. | 252/182.3 |
| 5,221,499 | A | * | 6/1993 | Klein et al. | 260/665 R |
| 5,779,942 | A | * | 7/1998 | Pelletier et al. | 260/665 R |
| 6,348,166 | B1 | * | 2/2002 | Knoll et al. | 260/665 R |

FOREIGN PATENT DOCUMENTS

EP   0 285 374 A   10/1988

* cited by examiner

*Primary Examiner*—Porfirio Nazario Gonzalez
(74) *Attorney, Agent, or Firm*—Fulbright & Jaworski LLP

(57) ABSTRACT

A diorganomagnesium-containing synthesis means, a method for its preparation and its use.

21 Claims, No Drawings

METHOD FOR PREPARING DIORGANOMAGNESIUM-CONTAINING SYNTHESIS MEANS

This application is a §371 of PCT/EP2006/067464 filed Oct. 16, 2006, which claims priority from German Patent Application No. DE 2005 049 635.0 filed Oct. 14, 2005, and German Patent Application No. DE 10 2006 024 915.1 filed May 24, 2006.

The present invention provides a diorganomagnesium-containing synthesis agent, a process for its preparation, and the use of this synthesis agent.

The present invention provides in particular a process for the preparation of mixtures of diorganomagnesium-containing synthesis agents with alkali salts for use in organic and organometallic synthetic chemistry, for example in halogen/metal exchange reactions or transmetallation reactions, or in metallation reactions.

Organomagnesium compounds are used in a variety of applications in chemical synthesis (H. G. Richey, Jr., Grignard Reagents New Developments, John Wiley and Sons, 2000; G. S. Silvermann, P. E. Rakita, Handbook of Grignard Reagents, Marcel Dekker Inc., 1996). In terms of reactivity, Grignard reagents RMgX and diorganomagnesium compounds $R^1R^2Mg$ are very similar (K. Nützel, Methoden der organischen Chemie, Metallorganische Verbindungen (Houben-Weyl, Ed.: E. Müller, O. Bayer), Thieme Verlag Stuttgart, 1973, Volume XIII/2a, Edition 4, p. 197ff.). Mixtures of diorganomagnesium compounds with alkali-metal organyls in some cases exhibit higher reactivity, which is readily made use of in synthetic chemistry (K. Kitigawa, A. Inoue, H. Shinokubo, K. Oshima, Angew. Chem. 2000, 112, 2594; A. Inoue, K. Kitagawa, H. Shinokubo, K. Oshima, J. Org. Chem. 2001, 66, 4333; A. Inoue, K. Kitagawa, H. Shinokubo, K. Oshima, Tetrahedron 2000, 56, 9601).

Accordingly, inter alia, mixtures of Grignard or dialkylmagnesium compounds and lithium chloride LiCl are disclosed as a highly potent reagent for halogen/metal exchange reactions. By reaction of these mixtures with, for example, aryl halides, new organomagnesium compounds are obtainable which cannot be prepared, or can be prepared only with difficulty, by other processes (P. Knochel et al., EP-A-04008081; P. Knochel et al., EP-A-1582524; P. Knochel et al., Angew. Chem. Int. Ed. 2003, 42, 4302; A. Krasovskiy et al., Angew. Chem. Int. Ed. 2004, 43, 3333; P. Knochel et al., Chem. Commun. 2004, 2288; P. Knochel et al., Org. Lett. 2004, 6, 4215; P. Knochel, Chem. Commun. 2005, 543; P. Knochel, Angew. Chem. Int. Ed. 2005, 44, 1654; P. Knochel et al., Angew. Chem. Int. Ed. 2005, 44, 3133).

The advantage of using such dialkylmagnesium/LiCl mixtures in halogen/metal exchange reactions instead of mixtures of alkylmagnesium halides and lithium chloride is that the rate of conversion is markedly higher, unactivated organic compounds can be converted and, in addition, only half the amount of dialkylmagnesium compound need be used, because both alkyl substituents are involved in the exchange reaction. The economy of a halogen/metal exchange reaction can therefore be increased considerably by using dialkylmagnesium/LiCl mixtures. However, the use of this method requires a diorganomagnesium compound to be available and to be mixed with a lithium salt.

However, the preparation of diorganomagnesium-containing synthesis agents, on the one hand, and the mixing thereof with alkali salts, on the other hand, is complex according to the prior art.

The known methods for the preparation of diorganomagnesium-containing synthesis agents are described hereinbelow.

The transmetallation of diorganomercury compounds with magnesium yields diorganomagnesium compounds, as shown in Scheme 1. However, a diorganomercury compound must be prepared and made available for this process. Such mercury compounds are additionally extremely toxic (H. C. Holtkamp et al., J. Organomet. Chem. 1969, 19, 279).

Scheme 1: Transmetallation reaction for the preparation of $R_2Mg$ compounds:

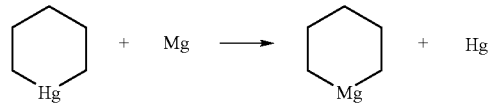

The reaction of organolithium compounds with organomagnesium halides yields diorganomagnesium compounds, with the formation of lithium halides, as shown in Scheme 2(C. W. Kamienski et al., J. Organomet. Chem. 1967, 8, 542). By using an excess of organolithium compounds or Grignard compounds, mixtures of diorganomagnesium compounds and lithium organyls or Grignard compounds are formed.

Scheme 2: Reaction of Grignard compounds with lithium organyls:

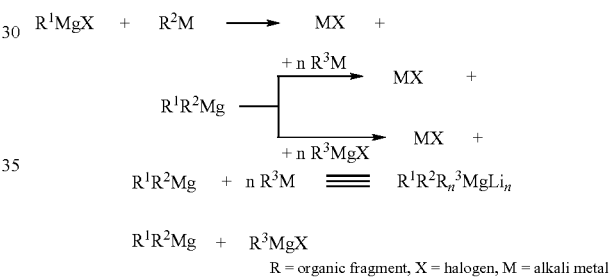

R = organic fragment, X = halogen, M = alkali metal

This method requires that a corresponding organolithium compound be available. However, many organolithium compounds are either not obtainable or have only limited stability in aprotic organic solvents or in ether-containing aprotic organic solvent mixtures. By the use of the above-described process, diorganomagnesium-containing synthesis agents are in most cases obtained in ether-containing solvent mixtures, which can impair the selectivity of a reaction in further reactions or can also impair the reactivity of the diorganomagnesium-containing synthesis agent. In some cases, depending on the coordination strength, the ether can be removed completely by distillation by addition of higher boiling hydrocarbons. This is possible, for example, in the preparation of dibutyl-(2)-magnesium. However, hydrocarbon has to be added continuously during the distillation. The preparation of diorganomagnesium compounds in only one solvent accordingly consumes a large amount of solvent and is therefore uneconomical.

Mixtures of, for example, di-(2)-butylmagnesium with lithium chloride for use in halogen/metal exchange reactions cannot be prepared directly by reaction of 2-butylmagnesium chloride with 2-butyllithium when commercially available dilute solutions of 2-butyllithium (12% in cyclohexane) and of 2-butylmagnesium chloride (25% in tetrahydrofuran (THF)) are used, because the lithium chloride that forms precipitates in the cyclohexane-rich solvent mixture and is accordingly no longer available for accelerating exchange reactions. If THF, for example, is added to this suspension, the lithium chloride that forms goes into solution, but the di-(2)-butylmagnesium/LiCl mixtures that are obtained are so dilute that their use in exchange reactions is uneconomical. Although a more concentrated solution of 2-butyllithium in, for example, cyclohexane can be used in order to obtain the desired di-(2)-butylmagnesium/LiCl mixtures directly, such concentrates are pyrophoric, have only limited stability and are difficult to handle. In addition, ether cleavage is observed in the presence of ethers even at lower temperatures, which leads to undesirable secondary products and losses in yield.

As is shown in Scheme 3, organomagnesium halides are present in solution according to W. Schlenk in the following equilibrium (W. Schlenk et al, Berichte 1929, 62, 920; W. Schlenk, Berichte 1931, 64, 734):

Scheme 3: Schlenk equilibrium:

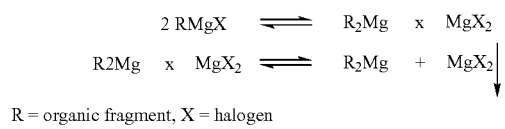

R = organic fragment, X = halogen

By the addition of specific solvents, such as, for example, pyridine, Crown ether, dioxan, tetramethylethylenediamine (TMEDA) or dimethyl ether (DME), the equilibrium is displaced in the direction towards the diorganomagnesium compound. After separation of the resulting poorly soluble magnesium halide, it is accordingly possible to obtain diorganomagnesium compounds or mixtures thereof with Grignard compounds, as is shown in Scheme 4.

Scheme 4: Diorganomagnesium compound via displacement of the Schlenk equilibrium:

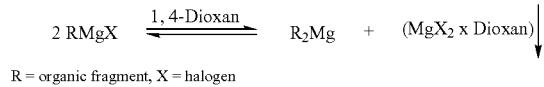

R = organic fragment, X = halogen

However, it is known that the displacement of the equilibrium is greatly dependent on the choice of solvent, the temperature, the time of action of the solvent on the Grignard compound, and the concentration of the solution. Almost complete precipitation of the magnesium halide is possible only with difficulty. It is therefore technically demanding to obtain definite products in a reproducible manner. In addition, this process requires the use of exotic solvents which are used only rarely commercially and some of which are toxic or carcinogenic.

Diorganomagnesium compounds can also be prepared by reaction of magnesium hydride MgH$_2$ with alkenes containing activated double bonds, as is shown in Scheme 5:

Scheme 5: Reaction of MgH$_2$ alkenes:

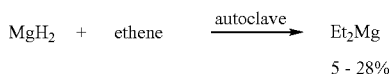

The yields of diorganomagnesium compounds prepared by this method are low. In addition, this process requires high pressures and temperatures. As a result, secondary reactions take place and the crude product must be purified in a technically complex manner.

A further method is described in EP-B-0285374. Mixtures of lithium organyls and diorganomagnesium compounds are obtained by reaction of an alkyl halide with a mixture of, for example, lithium and magnesium in hydrocarbons containing from 0.05 to 2 molar equivalents of a Lewis base per mol of organometallic composition, as is shown in Scheme 6:

Scheme 6: Mixtures of lithium organyls and diorganomagnesium compounds:

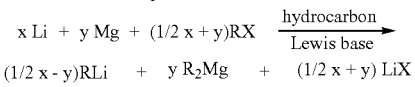

R = organic fragment, X = halogen
x > 2, y = 1

This process has the disadvantage that it is carried out in mixtures of hydrocarbons and Lewis bases, for example THF. The product is therefore present in a solvent mixture. This often has a disadvantageous effect in synthetic chemistry because, for example, changed selectivities or reactivities are obtained. In addition, it is known that if the amount of Lewis base exceeds or falls short of a specified amount, poorer yields are obtained, for example owing to secondary reactions such as ether cleavage. Because of the higher reactivity of lithium in comparison with magnesium, an organolithium compound mainly accumulates in the reaction mixture at the beginning of the reaction. It is known, however, that many organolithium compounds, such as, for example, sec-butyllithium, have only limited stability in solvents containing Lewis bases and react with the Lewis base. Undesirable secondary products thereby form, and the yield falls accordingly. The process therefore has only limited usability. In addition, because of the poor solubility of lithium salts in solvents containing only small amounts of Lewis base, only synthesis agents that are low in or free of lithium salts are obtained according to this process, and such synthesis agents are not suitable for use in halogen/metal exchange reactions, for example.

A further process is disclosed in U.S. Pat. No. 5,171,467. Here too, the reaction takes place in solvent mixtures of hydrocarbons and ethers. The process is explained by way of example by means of Scheme 7.

Scheme 7: Preparation of diorganomagnesium compounds via magnesium halides:

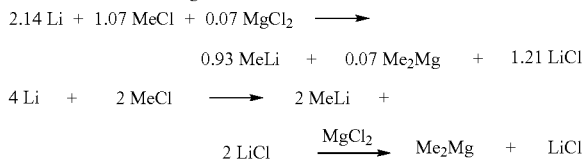

As is shown, an organolithium compound is formed as an intermediate in the synthesis and is subsequently reacted with magnesium chloride. Anhydrous magnesium chloride must therefore be used in the synthesis in order to prevent partial hydrolysis of the organolithium compound, which would lead to a loss in yield. Anhydrous magnesium chloride must be prepared in situ in a technically complex manner or must be dried at high temperatures for a long time. Both operations have a disadvantageous effect on the economy of this method.

In addition, a pure diorganomagnesium compound can be obtained only when an excess of dry magnesium halide is used. If magnesium halides are used in less than stoichiometric amounts, a mixture of a diorganomagnesium compound and a lithium organyl is formed.

As has already been described above, it is known that many lithium organyls have only limited stability in ether-containing solvent mixtures because of ether cleavage. Secondary reactions occur, which result in undesirable secondary products and poorer yields. The process therefore has only limited usability. Magnesium chloride is only sparingly soluble in mixtures of hydrocarbons and ethers, which results in a slower reaction of the organolithium compound with magnesium chloride. Long reaction times are necessary, which favours secondary reactions, for example ether cleavage. In addition, only diorganomagnesium-containing synthesis agents that are low in or free of lithium salts are obtained according to this process, which synthesis agents have only limited usability, as has been described.

In addition to these methods there are further methods, but these are suitable only for the synthesis of specific organomagnesium compounds. The direct preparation of organomagnesium compounds from magnesium and organic halides is possible only in rare cases. For example, it is possible in the case of di-(2)-butylmagnesium, butylethylmagnesium, butyloctylmagnesium, n-butyl-sec-butylmagnesium. However, these compounds can be prepared only under conditions which are very disadvantageous in terms of energy. For example, some of the alkyl halides used for the synthesis must be added under high pressure to the boiling suspension of solvent and very fine magnesium powder. Because secondary reactions also take place at the very high reaction temperatures, gaseous alkenes from β-H elimination reactions are always given off into the surroundings. For example, it is known that relatively large amounts of butene are formed in the synthesis of dibutylmagnesium. It is also known that some of the dialkylmagnesium compounds prepared in this manner have poor solubility in the solvent used. Therefore, octyl chloride must always be added where possible to form octyl-containing dialkylmagnesium compounds. Although the solubility of the compound is thereby increased, it is not possible to prepare a definite product in this manner. It is likewise known that solutions of the dialkylmagnesium compounds so prepared always have a very high viscosity, through the formation of coordination polymers, so that auxiliary agents such as aluminium alkyls must in principle be added in order to lower the viscosity. However, this impairs the purity considerably. In addition, long reaction times are necessary owing to the slow oxidative addition, shown in Scheme 8, of the two necessary equivalents of alkyl halide to magnesium (Magnesium Alkyls from Akzo Nobel, 1999: Metal Alkyls from Akzo Nobel, 2003; M. de Vries, Stamicarbon N. V. 1969, U.S. Pat. No. 3,737,393; Zn-Zusätze: G. W. Knight, L. Jackson, D. E. Mach, Dow Chemical Comp. 1975, U.S. Pat. No. 4,213,880; SiOR₄-Zusatz: Akzo Nobel 1997, WO-A-99/09035; GaR3, InR3, RLi: L. W. Fannin, D. B. Malpass, R. Sanchez; Texas Alkyls 1980, U.S. Pat. No. 4,299, 781; C. W. Kamiensky, B. J. McElroy, R. O. Bach, Lithium Corp. of America 1976 U.S. Pat. No. 4,069,267; L. W. Fannin, D. B. Malpass, Texas Alkyls 1977, U.S. Pat. No. 4,127,507; D. B. Malpass, D. W. Webb, Texas Alkyls 1984, U.S. Pat. No. 4,547,477).

Scheme 8: Synthesis of R₂Mg compounds from magnesium and organic halides using the example of di-(2)-butylmagnesium:

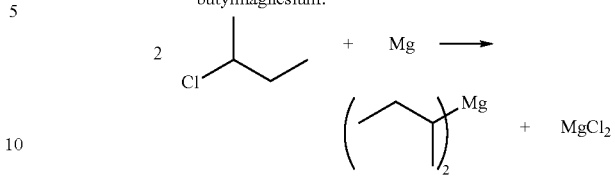

Mixtures of diorganomagnesium compounds and alkali-metal organyls are obtained according to Scheme 9 by reaction of diorganomagnesium compounds with alkali metals (D. B. Malpass, J. F. Eastham, J. Org. Chem. 1973, 21, 3718).

Figure 9: Mixtures of diorganomagnesium compounds and alkali-metal organyls:

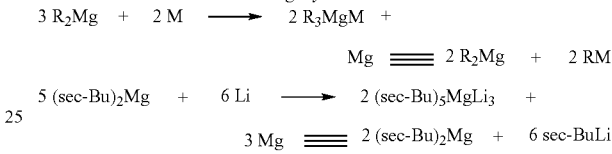

R = organic fragment, M = alkali metal

However, this process requires that a diorganomagnesium compound be available. As has been shown, however, the preparation of such compounds by methods of the prior art is difficult.

The speed of halogen/metal exchange reactions can be increased drastically by the use of, for example, mixtures of Grignard compounds or diorganomagnesium compounds with lithium salts. By the addition of lithium salts to the above-described compounds it is possible to prepare reagents which cannot be prepared commercially, or which can be prepared commercially only with difficulty, by other processes owing to secondary reactions or long reaction times. In all the above-described possible methods of preparing diorganomagnesium compounds that do not use lithium organyls or lithium metal as starting material, a lithium salt, for example lithium chloride, must therefore be added in a further process step. Because of the poor solubility of the lithium salt in the solvent or solvent mixture used, a solvent exchange must additionally be carried out in some cases.

If organomagnesium compounds are prepared via lithium organyls or using lithium metal, a lithium salt forms in situ. However, because it is necessary in the described processes to work in hydrocarbons or in ether/hydrocarbon mixtures owing to the implementability of the methods, the lack of stability or lack of solubility of the resulting lithium organyl, a large part of the lithium salt that forms precipitates. Although this can be brought into solution again by the addition of polar solvents, dilute solutions form, which are uneconomical to use in synthetic chemistry. In order nevertheless to obtain lithium-salt-containing mixtures, a solvent exchange is necessary in this case too in a further process step. In addition, the availability and stability of an organolithium compound are required in some cases.

Lithium chloride is very hygroscopic, which makes its subsequent introduction into organomagnesium compounds difficult. If water-containing or slightly moist lithium chloride is used, partial hydrolysis of the organomagnesium compounds takes place. Undesirable secondary products form as a result, and the yield of organomagnesium compounds falls accordingly.

All the mentioned processes for the preparation of diorganomagnesium-containing synthesis agents or mixtures thereof with alkali-metal salts are either expensive, require the handling of pyrophoric or even toxic compounds, use as starting materials organometallic compounds which in some cases are not available commercially or organometallic compounds which have only limited stability, require a plurality of process steps, lead to the formation of undesirable secondary products or have only limited usability. The object of providing an efficient, simple and inexpensive process, which can be carried out commercially, for the preparation of diorganomagnesium-containing synthesis agents and mixtures thereof with alkali salts has accordingly not hitherto been achieved.

The object of the present invention is, therefore, to provide a process for the preparation of diorganomagnesium-containing synthesis agents which overcomes the disadvantages of the prior art.

It is a particular object of the present invention to provide a process which yields identically or differently substituted diorganomagnesium-containing synthesis agents in only one specified solvent or in specified solvent mixtures, and which yields directly alkali-salt-containing solutions, but also solutions which are low in or free of alkali-metal salts, of diorganomagnesium-containing synthesis agents in specific solvents or solvent mixtures.

Surprisingly, the object is achieved according to the invention by the features of the main claim. Preferred embodiments will be found in the subsidiary claims.

Surprisingly, the process according to the invention permits the preparation of a large number of diorganomagnesium compounds, such as, for example, dialkyl-, dialkenyl-, dialkynyl-, diaryl-, diheteroaryl-, alkylalkenyl-, alkylalkynyl-, alkylaryl-, alkylheteroaryl-, alkenylalkynyl-, alkenylaryl-, alkenylheteroaryl-, alkynylaryl- or alkynylheteroaryl-magnesium compounds, or mixtures thereof with alkali-metal organyls or Grignard compounds, or mixtures with alkali-metal salts, in only one specific solvent or in specific solvent mixtures.

By means of the process according to the invention, alkali-salt-containing solutions of diorganomagnesium-containing synthesis agents or solutions that are low in or free of alkali-metal salts can also be prepared directly. The diorganomagnesium-containing synthesis agents prepared according to the invention, or mixtures thereof with alkali-metal salts, can be used in the preparation of a large number of in some cases highly functionalised substances, such as pharmaceuticals, natural substance derivatives, polymer materials, agrochemicals, specialty chemicals and catalysts, for example in halogen/metal exchange reactions or metallation reactions, for example ortho-metallation reactions, or transmetallation reactions, for example in the preparation of diorganozinc compounds or organozinc halides.

It has been found, surprisingly, that the desired diorganomagnesium-containing synthesis agents, or mixtures thereof with alkali-metal salts, are formed directly by reaction of a compound of the general formula RMgX—or of a plurality of compounds of the general formula $R^1MgX$, $R^2MgX$ and $R^3MgX$—and a compound of the general formula RX—or a plurality of compounds of the general formula $R^1X$, $R^2X$ and $R^3X$—with alkali metal or with a mixture of alkali metal and magnesium. This embodiment of the process according to the invention is explained by the general reaction formula in Scheme 10, without limiting the invention thereto.

Alkali metal within the scope of the invention is the pure alkali metal and also mixtures or alloys thereof with other alkali metals. Lithium or mixtures or alloys of lithium and another alkali metal, preferably sodium, are preferably used as the alkali metal. The content of lithium in the mixtures or alloys is from 50 to 99.99 wt. %, preferably from 80 to 99.99 wt. %, more preferably from 90 to 99.99 wt. %. However, other alkali metals can also be used.

The process according to the invention is explained in detail using the example of the following formula (Scheme 10):

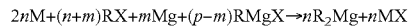

R=organic fragment, X=halogen; M=lithium or lithium-containing mixture or alloy

RMgX=Grignard compound or mixture of x•$R^1$MgX and y•$R^2$MgX Grignard compounds, wherein x+y=(p−m) and x and y are chosen independently of one another between 0 and (p−m)

RX=organic halide or mixture of x•$R^1$X and y•$R^2$X organic halides, wherein x+y=(n+m) and x and y are chosen independently of one another between 0 and (n+m)

The process according to the invention is generally carried out as follows:

The alkali metal or a mixture of alkali metal and magnesium is suspended in an aprotic organic solvent or solvent mixture. The desired diorganomagnesium-containing synthesis agent or a mixture thereof with alkali-metal salts is formed by addition of a Grignard compound RMgX—or of a plurality of Grignard compounds $R^1$MgX, $R^2$MgX and $R^3$MgX—and of a compound of the general formula RX—or of a plurality of compounds of the general formula $R^1$X, $R^2$X and $R^3$X—separately or mixed beforehand. The compounds of the general formulae $R^1$MgX, $R^2$MgX and $R^3$MgX are preferably added in solution in an aprotic organic solvent or solvent mixture, more preferably in the solvent or solvent mixture in which the alkali metal or the mixture of alkali metal and magnesium is suspended.

The molar ratio of the total amount of alkali metal to the total amount of compounds of the general formulae RX, $R^1$X, $R^2$X and $R^3$X is 2n/(n+m), the molar ratio of magnesium to the total amount of compounds of the general formulae RX, $R^1$X, $R^2$X and $R^3$X is m/(n+m) and the molar ratio of the total amount of compounds of the general formula RMgX, $R^1$MgX, $R^2$MgX and $R^3$MgX to the total amount of compounds of the general formulae RX, $R^1$X, $R^2$X and $R^3$X is (p−m)/(n+m), wherein n is chosen between n=0.1 and n=5, preferably between n=0.8 and n=3, and m is chosen between m=0 and m=5, preferably between m=0 and m=3, and wherein (p−m)>0 and p is chosen between p=0 and p=10, preferably between p=0 and p=6.

In a preferred embodiment according to the invention for the preparation of diorganomagnesium compounds and mixtures thereof with alkali-metal salts, n is chosen between n=0.8 and n=1.8, preferably between n=0.8 and n=1.2, and m is chosen between m=0 and m=1, preferably between m=0 and m=0.5, and p is chosen between p=0 and p=3, preferably between p=0 and p=1.5, wherein (p−m)>0.

In a preferred embodiment according to the invention for the preparation of mixtures of diorganomagnesium compounds and Grignard compounds and mixtures thereof with alkali-metal salts, p for n≧m is preferably p≧n and for n≦m p is preferably p≧m.

In a preferred embodiment according to the invention for the preparation of mixtures of diorganomagnesium compounds and alkali-metal organyls and mixtures thereof with alkali-metal salts, preferably n≧m and p≦n.

In a preferred embodiment according to the invention for the preparation of identically substituted diorganomagnesium-containing synthesis agents, a Grignard compound RMgX and an organic halide RX are used.

In a preferred embodiment according to the invention for the preparation of differently substituted diorganomagnesium-containing-synthesis agents, x•R$^1$MgX and y•R$^2$MgX Grignard compounds and organic halide z•R$^3$X are used, wherein x and y are chosen independently of one another between 0 and (p−m) and wherein the sum of x+y=(p−m) and wherein z is chosen between 0 and (n+m).

In a further preferred embodiment according to the invention for the preparation of differently substituted diorganomagnesium-containing synthesis agents, x•R$^1$X and y•R$^2$X organic halides and Grignard compound x•R$^3$MgX are used, wherein x and y are chosen independently of one another between 0 and (n+m) and wherein the sum of x+y=(n+m) and wherein z is chosen between 0 and (p−m).

In a further preferred embodiment according to the invention, the ratio of the molar rate of addition of the total amount of organic halides RX, R$^1$X, R$^2$X, R$^3$X to the molar rate of addition of the total amount of Grignard compounds RMgX, R$^1$MgX, R$^2$MgX, R$^3$MgX is from 1:50 to 50:1, preferably from 1:20 to 20:1, particularly preferably from 1:10 to 10:1, very particularly preferably from 1:5 to 5:1.

If rates of addition other than those specified above are chosen there is the possibility of secondary reactions such as, for example, ether cleavage, in particular when the organic halide is added markedly more rapidly than the Grignard compound.

Diorganomagnesium-containing synthesis agents within the scope of the invention are diorganomagnesium compounds R$_2$Mg or R$_x^1$R$_y^2$Mg and mixtures thereof with z Grignard compounds RMgX or R$^3$MgX or z alkali-metal organyls RM or R$^3$M. The molar mixing ratio with Grignard compounds or alkali-metal organyls is determined by z, z is in the range from 0 to 10, preferably from 0 to 4. The sum of the coefficients x and y is 2, and they are within the range between 0 and 2, independently of one another. R, R$^1$, R$^2$ and R$^3$ are chosen independently of one another and are as defined hereinbelow.

Depending on the solvent or solvent mixture used, mixtures of diorganomagnesium-containing synthesis agents and alkali salt halides are obtained that differ in terms of the ratio of alkali salt to organomagnesium compound.

Lithium or lithium-containing mixtures or alloys are preferably used in the form of a metal powder, a metal dispersion or metal granules, particularly preferably in the form of a metal powder or a metal dispersion.

Magnesium is preferably used in the form of turnings, flakes or powders.

Grignard compounds RMgX and organic halides RX are preferably added to a suspension of the alkali metal or of a mixture of alkali metal and magnesium in an aprotic organic solvent or solvent mixture.

For the preparation of the diorganomagnesium-containing synthesis agents according to the invention in solvent mixtures of ethers and hydrocarbons, one or more different Grignard compounds RMgX in ethers or in mixtures of ethers and hydrocarbons are used in a further embodiment. Furthermore, the alkali metal or the alkali metal and magnesium is preferably suspended in an aromatic or aliphatic hydrocarbon. The ethers used can be removed by methods of the prior art when the reaction is complete, for example by distillation under normal pressure, under reduced pressure, by vacuum distillation or by concentration by evaporation. Solutions of diorganomagnesium-containing synthesis agents that are low in or free of alkali-metal salts are thus formed.

For the preparation of diorganomagnesium-containing synthesis agents containing alkali-metal salts, for example for use in halogen/metal exchange reactions or metallation reactions, solely ethereal solvents are used in a preferred embodiment, preference being given to cyclic ethers and particularly preferably to THF and 2-methyl-THF.

The process for the preparation of diorganomagnesium-containing synthesis agents is preferably carried out with the exclusion of air and moisture, preferably in an inert gas atmosphere, particularly preferably in a nitrogen or argon atmosphere.

The process according to the invention can be carried out at temperatures from −−100° C. to the boiling point of the reaction suspension; it is preferably carried out in a temperature range from −15° C. to the boiling point of the reaction suspension, particularly preferably from 0° C. to 60° C.

The diorganomagnesium-containing synthesis agent according to the invention is obtained in addition to solids, which in a preferred embodiment are separated off by methods of the prior art. Methods of the prior art are, for example, decantation, filtration or centrifugation. The resulting solutions of diorganomagnesium-containing synthesis agents are either free of alkali-metal salt or contain alkali-metal salt, depending on the solvent or solvent mixture, and can be used directly in organic or organometallic synthetic chemistry.

In the Grignard compounds of the general composition RMgX, R$^1$MgX, R$^2$MgX and R$^3$MgX and in the organic halides RX, R$^1$X, R$^2$X and R$^3$X and in the diorganomagnesium compounds R$_2$Mg and R$_x^1$R$_y^2$Mg and mixtures thereof with alkali-metal organyls RM and R$^3$M or Grignard compounds RMgX and R$^3$MgX:

R, R$^1$, R$^2$ and R$^3$, which may be identical or different, can be selected from H, saturated, unsaturated, branched, unbranched, functionalised, unfunctionalised, aliphatic, cyclic, heterocyclic or aromatic organic fragments, preferably fragments having from 1 to 80, particularly preferably from 1 to 40, very particularly preferably from 1 to 20 carbon atoms, and R can generally also represent R$^1$, R$^2$ and R$^3$, and X is selected from chlorine, bromine, iodine, tosylate and triflate, preferably from chlorine, bromine and iodine, and M is an alkali metal.

In particular, R, R$^1$, R$^2$ and R$^3$, which may be identical or different, can be selected from methyl, ethyl, cyclopropyl, cyclopentyl, cyclohexyl, phenyl, benzyl and heteroaryl fragments as well as branched and unbranched propyl, butyl, pentyl, hexyl, heptyl, octyl fragments.

Preferred aprotic organic solvents are aliphatic or aromatic hydrocarbons, heterocycles, ethers, amines, nitriles or mixtures thereof.

Within the scope of the invention, the term aliphatic hydrocarbons includes cyclic, saturated, unsaturated, branched and unbranched hydrocarbons. Preference is given to saturated or cyclic, branched or unbranched hydrocarbons having from 5 to 20 carbon atoms, particularly preferably n-pentane, n-hexane, n-heptane, n-octane or the isomers thereof, cyclopentane, cyclohexane and methylcyclohexane.

Within the scope of the invention, the term ethers includes acyclic, cyclic, saturated, unsaturated, branched, unbranched, identically substituted and differently substituted ethers having at least one oxygen atom, preferably having from one to four oxygen atoms. Also preferred as ethers are dimethyl ether, diethyl ether, dibutyl ether, dimethoxyethane, diethoxymethane, polyethylene glycol, methyl tert-butyl ether, cyclopentyl methyl ether, dioxan, tetrahydrofuran and 2-methyl-tetrahydrofuran, and particular preference is given to THF and 2-methyl-THF.

Within the scope of the invention, the term amines includes acyclic, cyclic, saturated, unsaturated, branched, unbranched, identically substituted and differently substituted amines having at least one nitrogen atom, preferably having from one to four nitrogen atoms, preference being given to N,N-tetramethylethylenediamine.

Within the scope of the invention, the term aromatic hydrocarbons includes unsubstituted, monosubstituted and polysubstituted aromatic compounds. Benzene, toluene, ethylbenzene, cumene and xylene and the isomers thereof are preferably used.

Within the scope of the invention, heterocycles are substituted, unsubstituted, aromatic, saturated and unsaturated cyclic compounds which consist in the ring of at least four carbon atoms and at least one atom from the group of the heteroatoms oxygen, sulfur and nitrogen, preference being given to from four to six carbon atoms and from one to three heteroatoms, particular preference being given to pyridine, THF and 2-methyltetrahydrofuran.

In detail, the invention provides:

a process for the preparation of diorganomagnesium-containing synthesis agents and mixtures thereof with alkali-metal salts, characterised in that an alkali metal or mixtures or alloys of alkali metals, a Grignard compound of the general formula $RMgX$ or a plurality of Grignard compounds of the general formulae $R^1MgX$, $R^2MgX$ and $R^3MgX$, an organic halide of the general formula $RX$ or a plurality of organic halides of the general formulae $R^1X$, $R^2X$ and $R^3X$ are reacted with one another;

a process for the preparation of diorganomagnesium-containing synthesis agents and mixtures thereof with alkali-metal salts using alkali metals or mixtures or alloys of alkali metals, Grignard compounds of the general formula $RMgX$ and organic halides of the general formula $RX$, wherein the diorganomagnesium-containing synthesis agents are formed directly from the added reagents;

a process for the preparation of diorganomagnesium-containing synthesis agents and mixtures thereof with alkali-metal salts, wherein magnesium is additionally also used;

a process for the preparation of diorganomagnesium-containing synthesis agents and mixtures thereof with alkali-metal salts, wherein alkali metal is to be understood as being lithium or mixtures or alloys consisting of lithium and another alkali metal, preferably sodium, wherein the amount of lithium in the mixtures or alloys is from 50 to 99.99 wt. %, preferably from 80 to 99.99 wt. %, more preferably from 90 to 99.99 wt. %;

a process for the preparation of diorganomagnesium-containing synthesis agents and mixtures thereof with alkali-metal salts, wherein the alkali metal or the alkali metal and magnesium is/are suspended in an organic aprotic solvent or solvent mixture and a compound of the general formula $RMgX$ or a plurality of compounds of the general formulae $R^1MgX$, $R^2MgX$ and $R^3MgX$—separately or mixed beforehand—and a compound of the general formula $RX$ or a plurality of compounds of the general formulae $R^1X$, $R^2X$ and $R^3X$—separately or mixed beforehand—are added;

a process for the preparation of diorganomagnesium-containing synthesis agents and mixtures thereof with alkali-metal salts, wherein there are added compounds of the general formulae $RMgX$, $R^1MgX$, $R^2MgX$ and $R^3MgX$ dissolved in an aprotic organic solvent or solvent mixture, preferably in the solvent or solvent mixture in which the alkali metal or the alkali metal and magnesium is/are suspended;

a process for the preparation of diorganomagnesium-containing synthesis agents and mixtures thereof with alkali-metal salts, wherein the molar ratio of the total amount of alkali metal to the total amount of compounds of the general formulae $RX$, $R^1X$, $R^2X$ and $R^3X$ is $2n/(n+m)$, the molar ratio of magnesium to the total amount of compounds of the general formulae $RX$, $R^1X$, $R^2X$ and $R^3X$ is $m/(n+m)$ and the molar ratio of the total amount of compounds of the general formulae $RMgX$, $R^1MgX$, $R^2MgX$ and $R^3MgX$ to the total amount of compounds of the general formulae $RX$, $R^1X$, $R^2X$ and $R^3X$ is $(p-m)/(n+m)$, wherein n is chosen between $n=0.1$ and $n=5$, preferably between $n=0.8$ and $n=3$, and m is chosen between $m=0$ and $m=5$, preferably between $m=0$ and $m=3$, and $(p-m)>0$ and p is chosen between $p=0$ and $p=10$, preferably between $p=0$ and $p=6$;

a process for the preparation of diorganomagnesium-containing synthesis agents and mixtures thereof with alkali-metal salts, wherein in a preferred embodiment for the preparation of diorganomagnesium compounds and mixtures thereof with alkali-metal salts n is chosen between $n=0.8$ and $n=1.8$, preferably between $n=0.8$ and $n=1.2$, and m is chosen between $m=0$ and $m=1$, preferably between $m=0$ and $m=0.5$, and $(p-m)>0$ and p is chosen from a range between $p=0$ and $p=3$, preferably between $p=0$ and $p=1.5$;

a process for the preparation of diorganomagnesium-containing synthesis agents and mixtures thereof with alkali-metal salts, wherein for the preparation of mixtures of diorganomagnesium compounds and Grignard compounds and mixtures thereof with alkali-metal salts for $n \geq m$ preferably $p \geq n$ and for $n \leq m$ preferably $p \geq m$;

a process for the preparation of diorganomagnesium-containing synthesis agents and mixtures thereof with alkali-metal salts, wherein for the preparation of mixtures of diorganomagnesium compounds and alkali-metal organyls and mixtures thereof with alkali-metal salts $n \geq m$ and $p \leq n$;

a process for the preparation of identically substituted diorganomagnesium-containing synthesis agents and mixtures thereof with alkali-metal salts, wherein a Grignard compound $RMgX$ and an organic halide $RX$ are used;

a process for the preparation of differently substituted diorganomagnesium-containing synthesis agents and mixtures thereof with alkali-metal salts, wherein there are used for the preparation $x \cdot R^1MgX$ and $y \cdot R^2MgX$ Grignard compounds and organic halide $z \cdot R^3X$, wherein x and y are chosen independently of one another between 0 and $(p-m)$ and wherein the sum of $x+y=(p-m)$ and wherein z is chosen between 0 and $(n+m)$ and wherein $R^1=R^2 \neq R^3$ or $R^1=R^3 \neq R^2$ or $R^2=R^3 \neq R^1$ or $R^1 \neq R^2 \neq R^3$;

a process for the preparation of differently substituted diorganomagnesium-containing synthesis agents and mixtures thereof with alkali-metal salts, wherein there are used for the preparation $x \cdot R^1X$ and $y \cdot R^2X$ organic halides and Grignard compound $z \cdot R^3MgX$, wherein x and y are chosen independently of one another between 0 and $(n+m)$ and wherein the sum of $x+y=(n+m)$ and wherein z is chosen between 0 and $(p-m)$ and wherein $R^1=R^2 \neq R^3$ or $R^1=R^3 \neq R^2$ or $R^2=R^3 \neq R^1$ or $R^1 \neq R^2 \neq R^3$;

a process for the preparation of diorganomagnesium-containing synthesis agents and mixtures thereof with alkali-metal salts, wherein the ratio of the rate of addition of the total amount of organic halides RX, R$^1$X, R$^2$X, R$^3$X to the rate of addition of the total amount of Grignard compounds RMgX, R$^1$MgX, R$^2$MgX, R$^3$MgX is chosen between 1:50 and 50:1, preferably between 1:20 and 20:1, particularly preferably between 1:10 and 10:1, very particularly preferably between 1:5 and 5:1;

a process for the preparation of diorganomagnesium-containing synthesis agents and mixtures thereof with alkali-metal salts, wherein the lithium or the lithium-containing alloys or mixtures are used in the form of a metal powder, a metal dispersion or metal granules, preferably in the form of a metal powder or a metal dispersion;

a process for the preparation of diorganomagnesium-containing synthesis agents and mixtures thereof with alkali-metal salts, wherein the magnesium is preferably used in the form of turnings, flakes or powders;

a process for the preparation of diorganomagnesium-containing synthesis agents and mixtures thereof with alkali-metal salts, wherein the Grignard compounds RMgX or R$^1$MgX, R$^2$MgX and/or R$^3$MgX and the organic halides RX or R$^1$X, R$^2$X and/or R$^3$X are added to a suspension of the alkali metal or of the alkali metal and magnesium;

a process for the preparation of diorganomagnesium-containing synthesis agents and mixtures thereof with alkali-metal salts in solvent mixtures of ethers and hydrocarbons, wherein there are used for the preparation one or more different Grignard compounds RMgX or R$^1$MgX, R$^2$MgX and/or R$^3$MgX in ethers or, preferably, in mixtures of ethers and hydrocarbons and wherein the alkali metal or the alkali metal and magnesium is/are preferably suspended in an aromatic or aliphatic hydrocarbon, and wherein, when the reaction is complete, the ethers used can be removed by methods of the prior art, for example by distillation under normal pressure, under reduced pressure, by vacuum distillation or by concentration by evaporation, and wherein solutions of organomagnesium compounds that are low in or free of alkali-metal salts are formed;

a process for the preparation of diorganomagnesium-containing synthesis agents and mixtures thereof with alkali-metal salts, wherein for the preparation of diorganomagnesium-containing synthesis agents containing alkali-metal salts, for example for use in halogen/metal exchange reactions or metallation reactions, there are used solely ethereal solvents, preference being given to the use of cyclic ethers and particularly preferably THF and 2-methyl-THF;

a process for the preparation of diorganomagnesium-containing synthesis agents and mixtures thereof with alkali-metal salts, wherein the processes are carried out with the exclusion of air and moisture, preferably in an inert gas atmosphere, particularly preferably in a nitrogen or argon atmosphere;

a process for the preparation of diorganomagnesium-containing synthesis agents and mixtures thereof with alkali-metal salts, wherein the process according to the invention is carried out at temperatures of from −100° C. to the boiling point of the reaction suspension, preferably at temperatures of from −15° C. to the boiling point of the reaction suspension, particularly preferably from 0° C. to 60° C.;

a process for the preparation of diorganomagnesium-containing synthesis agents and mixtures thereof with alkali-metal salts, wherein the corresponding diorganomagnesium-containing synthesis agents and mixtures thereof with alkali-metal salts are separated from precipitated solids by methods of the prior art, preferably decantation, filtration or centrifugation;

a process for the preparation of diorganomagnesium-containing synthesis agents and mixtures thereof with alkali-metal salts, wherein R, R$^1$, R$^2$ and R$^3$ are in all cases selected independently of one another from H, saturated, unsaturated, branched, unbranched, functionalised, unfunctionalised, aliphatic, cyclic, heterocyclic or aromatic organic fragments, wherein in particular saturated, unsaturated, branched, unbranched, functionalised, unfunctionalised, aliphatic, cyclic, heterocyclic or aromatic organic fragments having from 1 to 80 carbon atoms are preferred, wherein saturated, unsaturated, branched, unbranched, functionalised, unfunctionalised, aliphatic, cyclic, heterocyclic or aromatic organic fragments having from 1 to 40 carbon atoms are preferred, wherein saturated, unsaturated, branched, unbranched, functionalised, unfunctionalised, aliphatic, cyclic, heterocyclic or aromatic organic fragments having from 1 to 20 carbon atoms are particularly preferred, and wherein branched and unbranched methyl, ethyl, propyl, butyl, pentyl, hexyl, heptyl, octyl, cyclopropyl, cyclopentyl, cyclohexyl, phenyl, benzyl and heteroaryl fragments are particularly preferred, and X is selected from chlorine, bromine, iodine, tosylate and triflate, preferably from chlorine, bromine and iodine;

a process for the preparation of diorganomagnesium-containing synthesis agents and mixtures thereof with alkali-metal salts, wherein aprotic organic solvents are used;

a process for the preparation of diorganomagnesium-containing synthesis agents and mixtures thereof with alkali-metal salts, wherein aliphatic or aromatic hydrocarbons, heterocycles, ethers, amines, nitriles or mixtures thereof are used;

a process for the preparation of diorganomagnesium-containing synthesis agents and mixtures thereof with alkali-metal salts, wherein there are used as aliphatic hydrocarbons cyclic, saturated, unsaturated, branched and unbranched hydrocarbons, preferably saturated or cyclic, branched or unbranched hydrocarbons having from 5 to 20 carbon atoms, particularly preferably n-pentane, n-hexane, n-heptane, n-octane or the isomers thereof, cyclopentane, cyclohexane and methylcyclohexane;

a process for the preparation of diorganomagnesium-containing synthesis agents and mixtures thereof with alkali-metal salts, wherein there are used as ethers cyclic, saturated, unsaturated, branched, unbranched, identically substituted and differently substituted ethers having at least one oxygen atom, preferably having from one to four oxygen atoms, particularly preferably dimethyl ether, diethyl ether, dibutyl ether, dimethoxyethane, diethoxymethane, methyl tert-butyl ether, polyethylene glycol, cyclopentyl methyl ether, dioxan, tetrahydrofuran and 2-methyltetrahydrofuran;

a process for the preparation of diorganomagnesium-containing synthesis agents and mixtures thereof with alkali-metal salts, wherein there are used as amines cyclic, aliphatic, saturated, unsaturated, branched, unbranched, identically substituted and differently substituted amines having at least one nitrogen atom, preferably having from one to four nitrogen atoms, particular preference being given to N,N-tetramethylethylenediamine;

a process for the preparation of diorganomagnesium-containing synthesis agents and mixtures thereof with alkali-metal salts, wherein there are used as aromatic hydrocarbons unsubstituted, monosubstituted and polysubstituted aromatic compounds, preferably benzene, toluene, ethylbenzene, cumene and/or xylenes or the isomers thereof;

a process for the preparation of diorganomagnesium-containing synthesis agents and mixtures thereof with alkali-metal salts, wherein there are used as heterocycles substituted, unsubstituted, aromatic, saturated and unsaturated cyclic compounds which consist in the ring of at least four carbon atoms, preferably from four to six carbon atoms, and at least one atom, preferably from one to three atoms, from the group of the heteroatoms oxygen, sulfur and nitrogen, wherein THF, 2-methyl-THF and pyridine are particularly preferred;

a process for the preparation of identically or differently substituted dialkyl-, dialkenyl-, dialkynyl-, diaryl-, diheteroaryl-, alkylalkenyl-, alkylalkynyl-, alkylaryl-, alkylheteroaryl-, alkenylalkynyl-, alkenylaryl-, alkenylheteroaryl-, alkynylaryl- or alkynylheteroaryl-magnesium compounds or mixtures thereof with alkali salts, Grignard compounds RMgX or organolithium compounds RLi;

a process for the preparation of identically or differently substituted di-n-alkyl-, di-sec-alkyl-, di-iso-alkyl-, di-tert-alkyl-, di-cycloalkyl-, di-aryl- and di-heteroaryl-magnesium compounds or mixtures thereof with alkali salts, Grignard compounds RMgX or organolithium compounds RLi;

a process for the preparation of dimethylmagnesium, diethylmagnesium, di-isopropylmagnesium, di-n-propylmagnesium, di-n-butylmagnesium, di-sec-butylmagnesium, di-isobutylmagnesium, di-tert-butylmagnesium, di-cyclo-propylmagnesium, di-cyclopentylmagnesium, di-cyclo-hexylmagnesium, di-n-pentylmagnesium, di-n-hexylmagnesium, diphenylmagnesium, dibenzylmagnesium, n-butyl-n-octylmagnesium, n-butyl-ethylmagnesium, s-butyl-ethylmagnesium or s-butyl-n-butylmagnesium or mixtures thereof with alkali salts, Grignard compounds RMgX or organolithium compounds RLi;

the use of the diorganomagnesium-containing synthesis agents prepared according to the invention, and of mixtures thereof with alkali salts, in synthetic chemistry;

the use of the diorganomagnesium-containing synthesis agents prepared according to the invention, and of mixtures thereof with alkali salts, in organic chemistry and organometallic chemistry;

the use of the diorganomagnesium-containing synthesis agents prepared according to the invention, and of mixtures thereof with alkali salts, in halogen/metal exchange reactions;

the use of the diorganomagnesium-containing synthesis agents prepared according to the invention, and of mixtures thereof with alkali salts, in metallation reactions, preferably in ortho-metallation reactions;

the use of the diorganomagnesium-containing synthesis agents prepared according to the invention, and of mixtures thereof with alkali salts, in transmetallation reactions;

the use of the diorganomagnesium-containing synthesis agents prepared according to the invention, and of mixtures thereof with alkali salts, in the preparation of organozinc halides or diorganozinc compounds;

the use of the diorganomagnesium-containing synthesis agents prepared according to the invention, and of mixtures thereof with alkali salts, in the preparation of magnesium alcoholates and magnesium halides;

a diorganomagnesium compound $R_x^1 R_y^2 Mg$ in the form of a solution in an ether-containing solvent, wherein it is present in admixture with lithium halides and/or Grignard compounds RMgX and/or alkali-metal organyls RM and the molar ratio of diorganomagnesium compounds to lithium halide is from 1:0.1 to 1:2 and the molar mixing ratio of diorganomagnesium compound and Grignard compound or alkali-metal organyl is from 1:0.15 to 1:4 and the sum of x+y=2 and x and y are chosen independently of one another from the range between 0 and 2;

a solution of diorganomagnesium compounds $R_x^1 R_y^2 Mg$ and lithium halides selected from the group lithium chloride, lithium bromide and lithium iodide in a tetrahydrofuran- or 2-methyltetrahydrofuran-containing solvent, and mixtures thereof with Grignard compounds RMgX or alkali-metal organyls RM, wherein R, $R^1$ and $R^2$ are chosen independently of one another from secondary alkyl groups, preferably sec-butyl, isopropyl, cyclopropyl, cyclopentyl, cyclohexyl, and the molar ratio of $R_x^1 R_y^2 Mg$ to the lithium halide is in the range from 1:0.1 to 1:2 and the molar mixing ratio of diorganomagnesium compound and Grignard compound or alkali-metal organyl is from 1:0.15 to 1:4 and the sum x+y=2 and x and y are chosen independently of one another from the range between 0 and 2;

a solution of diorganomagnesium compounds $R_x^1 R_y^2 Mg$ and lithium halides selected from the group lithium chloride, lithium bromide and lithium iodide in a tetrahydrofuran- or 2-methyltetrahydrofuran-containing solvent, and mixtures thereof with Grignard compounds RMgX or alkali-metal organyls RM, wherein R, $R^1$ and $R^2$ are chosen independently of one another from methyl, ethyl, isopropyl, n-propyl, n-butyl, isobutyl, sec-butyl, tert-butyl, n-pentyl, n-hexyl, n-heptyl, n-octyl, cyclopropyl, cyclopentyl, cyclohexyl, phenyl, benzyl, and the molar ratio of $R_x^1 R_y^2 Mg$ to the lithium halide is in the range from 1:0.1 to 1:2 and the molar mixing ratio of diorganomagnesium compound and Grignard compound or alkali-metal organyl is from 1:0.15 to 1:4 and the sum x+y=2 and x and y are chosen independently of one another from the range between 0 and 2;

a solution of diorganomagnesium compounds $R_x^1 R_y^2 Mg$ and lithium halides selected from the group lithium chloride, lithium bromide and lithium iodide in tetrahydrofuran or 2-methyltetrahydrofuran, and mixtures thereof with Grignard compounds RMgX or alkali-metal organyls RM, wherein R, $R^1$ and $R^2$ are chosen independently of one another from methyl, ethyl, isopropyl, n-propyl, n-butyl, isobutyl, sec-butyl, tert-butyl, n-pentyl, n-hexyl, n-heptyl, n-octyl, cyclopropyl, cyclopentyl, cyclohexyl, phenyl, benzyl, and the molar ratio of $R_x^1 R_y^2 Mg$ to the lithium halide is in the range from 1:0.1 to 1:2 and the molar mixing ratio of diorganomagnesium compound and Grignard compound or alkali-metal organyl is from 1:0.15 to 1:4 and the sum x+y=2 and x and y are chosen independently of one another from the range between 0 and 2;

a solution of diorganomagnesium compounds $R_x^1 R_y^2 Mg$ and lithium halides selected from the group lithium chloride, lithium bromide and lithium iodide in solvent mixtures of hydrocarbons and ethers, and mixtures thereof with Grignard compounds RMgX or alkali-metal organyls RM, wherein R, $R^1$ and $R^2$ are chosen independently of one another from methyl, ethyl, isopropyl, n-propyl, n-butyl, isobutyl, sec-butyl, tert-butyl, n-pentyl, n-hexyl, n-heptyl, n-octyl, cyclopropyl, cyclopentyl, cyclohexyl, phenyl, benzyl, and the molar ratio of $R_x^1R_y^2Mg$ to the lithium halide is in the range from 1:0.05 to 1:2 and the molar mixing ratio of diorganomagnesium compound and Grignard compound or alkali-metal organyl is from 1:0.05 to 1:4 and the sum x+y=2 and x and y are chosen independently of one another from the range between 0 and 2, and wherein the molar ratio of ether to diorganomagnesium compound is from 0.02:1 to 50:1;

a solution of diorganomagnesium compounds $R_x^1R_y^2Mg$ and lithium halides selected from the group lithium chloride, lithium bromide and lithium iodide in solvent mixtures of dimethyl ether, diethyl ether, dibutyl ether, methyl tert-butyl ether, cyclopentyl methyl ether, tetrahydrofuran or 2-methyltetrahydrofuran and toluene, cumene, xylenes, pentane, hexane, heptane, octane, cyclohexane or methylcyclohexane, and mixtures thereof with Grignard compounds RMgX or alkali-metal organyls RM, wherein R, $R^1$ and $R^2$ are chosen independently of one another from methyl, ethyl, isopropyl, n-propyl, n-butyl, isobutyl sec-butyl, tert-butyl, n-pentyl, n-hexyl, n-heptyl, n-octyl, cyclopropyl, cyclopentyl, cyclohexyl, phenyl, benzyl, and the molar ratio of $R_x^1R_y^2Mg$ to the lithium halide is in the range from 1:0.05 to 1:2 and the molar mixing ratio of diorganomagnesium compound and Grignard compound or alkali-metal organyl is from 1:0.05 to 1:4 and the sum x+y=2 and x and y are chosen independently of one another from the range between 0 and 2, and wherein the molar ratio of ether to diorganomagnesium compound is from 0.02:1 to 50:1.

The invention is explained by means of the following examples, without being limited thereto.

To illustrate the efficiency of the process according to the invention, the preparation of di-sec-butylmagnesium and mixtures thereof with sec-BuLi or sec-BuMgCl and LiCl is chosen. The preparation of this compound according to the prior art, for example by oxidative addition of two equivalents of sec-butyl chloride to magnesium, leads, as has been described, to β-H elimination and various secondary products. In addition, high process temperatures and long reaction times are necessary. Tests for the preparation of (sec-Bu)$_2$Mg by transmetallation with sec-BuLi result in solvent mixtures. If lithium-chloride-containing solutions are to be obtained directly by reaction of sec-BuMgCl with sec-BuLi, it is necessary to work with sec-BuLi concentrate, which has only limited stability and is also pyrophoric. If the synthesis of sec-Bu$_2$Mg/LiCl mixtures with sec-BuMgCl and sec-BuLi concentrate is carried out in THF at 0° C., for example, THF cleavage is additionally observed, so that the product solution is contaminated.

All tests are carried out in an argon atmosphere using Schlenk techniques. Commercial raw materials were used. With regard to sec-BuMgCl, various batches in the form of approximately 25% solutions in THF are used. The precise content and the composition of the batches are determined by wet analysis. With regard to lithium, lithium metal having different sodium contents was used. The sodium content is shown in Scheme 1, Table 1.

The test parameters, analytical results and evaluations of the examples relating to the preparation according to the invention of organomagnesium compounds are summarised in Schemes 1 and 2, Tables 1 and 2. In the examples, R=sec-butyl.

Where indicated, samples were taken during the reaction and examined by wet analysis. This was not taken into account when determining the yield, so that where samples were taken, the yields indicated in the tables are lower according to the number of samples.

The magnesium content was determined by complexometry, the chloride content by argentometry and the total base content by acidimetry after hydrolysis. The active base was determined according to Watson-Eastham using 2,2'-biquinoline as indicator.

EXAMPLES 1 TO 13

Diorganomagnesium-containing synthesis agents via lithium, sec-butyl chloride and sec-butylmagnesium chloride, in some cases with magnesium, according to Scheme 10

General Procedure Described by Means of Example 1

24.0 g (259 mmol) of sec-butyl chloride and 81.0 g (166 mmol) of sec-butylmagnesium chloride (in the form of an approximately 25% solution in THF) are added in the course of 125 minutes, at a reaction temperature of 25° C., to a suspension of 3.00 g (432 mmol) of lithium metal and 1.73 g (71 mmol) of coarse magnesium powder in 149 g of THF. After a post-reaction time of 60 minutes at 25° C., the resulting suspension is filtered and the residue is washed with THF and then dried in vacuo.

Yield original solution: 221.4 g of a brown solution; washing solution: 86.44 g.

Examples 2 to 13 were carried out analogously to Example 1 according to the experimental parameters indicated in Table 1. No magnesium metal was used in Examples 3 to 13. The test parameters and results are summarised in Table 2.

The identity and purity of the isolated products were confirmed by GC/MS investigations and $^1$H-NMR measurements.

TABLE 1

Test conditions in syntheses of diorganomagnesium-containing synthesis agents: Examples 1 to 13

| | Weighed amounts | | | | | Rates of addition | | | |
| --- | --- | --- | --- | --- | --- | --- | --- | --- | --- |
| Example | sec-BuMgCl[1] [mmol] | Li [mmol] | Mg [mmol] | sec-BuCl [mmol] | Solvent [g] | Temp. [° C.] | sec-BuCl [mmol/h] | sec-BuMgCl [mmol/h] | Post-reaction time [min] | Na content [wt. %] |
| 1 | 166 | 432 | 71 | 259 | 149[2] | 25 | 156 | 83 | 60 | 3.3 |
| 2 | 114 | 476 | 144 | 357 | 189[2] | 25 | 214 | 57 | 90 | 0.8 |
| 3 | 247 | 1130 | — | 494 | 115[2] | 35 | 228 | 239 | 120 | 3.8 |

TABLE 1-continued

Test conditions in syntheses of diorganomagnesium-containing synthesis agents: Examples 1 to 13

| | Weighed amounts | | | | | | Rates of addition | | | |
|---|---|---|---|---|---|---|---|---|---|---|
| Example | sec-BuMgCl[1] [mmol] | Li [mmol] | Mg [mmol] | sec-BuCl [mmol] | Solvent [g] | Temp. [°C.] | sec-BuCl [mmol/h] | sec-BuMgCl [mmol/h] | Post-reaction time [min] | Na content [wt. %] |
| 4 | 119 | 249 | — | 125 | 77[2] | 25 | 63 | 60 | 60 | 3.8 |
| 5 | 186 | 389 | — | 195 | 115[2] | 25 | 117 | 93 | 60 | 3.8 |
| 6 | 390 | 777 | — | 388 | 240[2] | 30 | 240 | 261 | 210 | 5.2 |
| 7 | 390 | 775 | — | 390 | 247[2] | 30 | 239 | 261 | 45 | 3.3 |
| 8 | 445 | 979 | — | 451 | 231[2] | 30 | 288 | 284 | 100 | 3.7 |
| 9 | 440 | 933 | — | 443 | 248[2] | 30 | 295 | 352 | >80 | 3.7 |
| 10 | 2226 | 5090 | — | 2250 | 1138[2] | 20-30 | 1055 | 1113 | 110 | 3.7 |
| 11 | 328 | 705 | — | 334 | 169[2] | 10 | 143 | 165 | 150 | 3.6 |
| 12 | 394 | 860 | — | 396 | 240[3] | 20 | 240 | 250 | 100 | 1.1 |
| 13 | 502 | 2170 | — | 998 | 350[3] | 25 | 230 | 230 | 150 | 2.5 |

[1] $[OH^-]$ = 2.05 mmol/g, $[Mg^{2+}]$ = 2.15 mmol/g, $[Cl^-]$ = 2.26 mmol/g; active base = 2.05 mmol/g;
[2] THF;
[3] toluene

TABLE 2

Analytical values and evaluation of the product solutions in syntheses of diorganomagnesium-containing synthesis agents: Examples 1 to 13

| | Analytical values | | | | Composition | | | | | | Yield |
|---|---|---|---|---|---|---|---|---|---|---|---|
| No. | OH [mmol/g] | Cl [mmol/g] | Mg [mmol/g] | Li [mmol/g] | LiCl [mmol/g] | RMgX[3] [mmol/g] | $R_2Mg$[4] [mmol/g] | RLi[5] [mmol/g] | | Active base [mmol/g] | (on OH) [%] |
| 1 | 1.55 | 1.06 | 0.82 | 0.99 | 0.99[1] | 0.07 | 0.75 | — | $R_2Mg \times 0.09\ RMgX \times 1.32\ LiCl$ | 1.56 | 84.8[6] |
| 2 | 1.57 | 1.00 | 0.80 | 0.98 | 0.98[1] | 0.02 | 0.78 | — | $R_2Mg \times 0.03\ RMgX \times 1.26\ LiCl$ | n.a. | 82.2[6] |
| 3 | 2.78 | 1.04 | 0.89 | 2.00 | 1.04 | — | 0.89 | 0.96 | $R_2Mg \times 1.08\ RLi \times 1.17\ LiCl$ | 2.74 | 93.0[6,7] |
| 4 | 1.68 | 1.27 | 0.88 | 1.15 | 1.15[1] | 0.12 | 0.76 | — | $R_2Mg \times 0.16\ RMgX \times 1.51\ LiCl$ | 1.53 | 99.7[7] |
| 5 | 1.69 | 1.22 | 0.93 | 1.10 | 1.10[1] | 0.12 | 0.81 | — | $R_2Mg \times 0.15\ RMgX \times 1.36\ LiCl$ | 1.67 | 96.6[8] |
| 6 | 1.40 | 1.20 | 0.80 | 1.08 | 1.08[1] | 0.12 | 0.68 | — | $R_2Mg \times 0.18\ RMgX \times 1.59\ LiCl$ | 1.32 | 93.6[8] |
| 7 | 1.59 | 1.25 | 0.85 | 1.14 | 1.14[1] | 0.11 | 0.74 | — | $R_2Mg \times 0.15\ RMgX \times 1.54\ LiCl$ | n.a. | 98.8[7] |
| 8 | 1.98 | 1.01 | 0.98 | 1.00 | 1.00[1] | 0.01 | 0.97 | — | $R_2Mg \times 0.01\ RMgX \times 1.03\ LiCl$ | n.a. | 98.9[7] |
| 9 | 1.82 | 1.11 | 0.90 | 1.12 | 1.11[2] | — | 0.90 | 0.01 | $R_2Mg \times 0.01\ RLi \times 1.23\ LiCl$ | 1.78 | 99.4[7] |
| 10 | 1.91 | 1.04 | 0.92 | 1.12 | 1.04[2] | — | 0.92 | 0.08 | $R_2Mg \times 0.09\ RLi \times 1.13\ LiCl$ | 1.88 | 97.9[7] |
| 11 | 1.88 | 1.05 | 0.92 | 1.11 | 1.05[2] | — | 0.92 | 0.06 | $R_2Mg \times 0.07\ RLi \times 1.14\ LiCl$ | n.a. | 93.4[8] |
| 12 | 1.51 | 0.51 | 0.74 | 0.54 | 0.51[2] | — | 0.74 | 0.03 | $R_2Mg \times 0.04\ RLi \times 0.69\ LiCl$ | 1.47 | 98.6[7] |
| 13 | 2.46 | 0.78 | 0.81 | 1.62 | 0.78[2] | — | 0.81 | 0.84 | $R_2Mg \times 1.04\ RLi \times 0.96\ LiCl$ | 2.41 | 97.8[7] |

[1] as [Li];
[2] as [Cl];
[3] calculated: [Cl]—[Li];
[4] calculated: $[Mg]_{tot}-[Mg]_{RMgX}$;
[5] calculated: [Li]—[Cl];
[6] sample removal not taken into account;
[7] washing solution taken into account;
[8] washing solution not taken into account

The invention claimed is:

1. A process for the preparation of diorganomagnesium-containing synthesis agents and mixtures thereof with alkali-metal salts comprising reacting an alkali metal or an alloy thereof with at least one Grignard compound of formula $RMgX_2$, $R^1MgX$ or $R^2MgX$ and at least one organic halide of formula RX, $R^1X$ or $R^2X$, wherein R, $R^1$ or $R^2$ are independently selected from the group consisting of methyl, ethyl, cyclopropyl, cyclopentyl, cyclohexyl, phenyl, benzyl, heteroaryl, propyl, butyl, pentyl, hexyl, heptyl and octyl, wherein the propyl, butyl, pentyl, heptyl and octoyl are branched or unbranched, and X is chlorine, bromine, iodine, tosylate or triflate.

2. A process according to claim 1, wherein magnesium is additionally added.

3. A process according to claim 1, wherein the alkali metal is lithium or a mixture or alloy containing lithium and another alkali metal, wherein the amount of lithium present is from 50 to 99.99 wt. %.

4. A process according to claim 1, wherein the molar ratio of the total amount of alkali metal to the total amount of compounds of the general formula RX is 2n/(n+m), the molar ratio of magnesium to the total amount of compounds of the general formula RX is m/(n+m), and the molar ratio of the total amount of compound RMgX to the total amount of compound RX is (p−m)/(n+m), wherein n is chosen between 0.1 and 5 and m is between 0 and 53, and (p−m)>0 wherein p is between 0 and 10.

5. A process according to claim 1, wherein n is between 0.8 and 1.8, m is between 0 and 1, and p is between 0 and 3.

6. A process according to claim 1, wherein for n>m.

7. A process according to claim 1, wherein n>m and p >n.

8. A process according to claim 1, wherein for the preparation of identically substituted diorganomagnesium-containing synthesis agents and mixtures thereof with alkali-metal salts there are used a Grignard compound RMgX and an organic halide RX.

9. A synthesis agent according to claim 2 wherein:
the lithium halides are chosen from the group lithium chloride, lithium bromide and lithium iodide;
the solvent is chosen from dimethyl ether, diethyl ether, dibutyl ether, methyl tert-butyl ether, cyclopentyl methyl ether, tetrahydrofuran, 2-methyltetrahydrofuran, toluene, cumene, xylenes, pentane, hexane, heptane, octane, cyclohexane and methylcyclohexane or any desired mixtures of at least two of these substances, and
R, $R^1$ and $R^2$ are chosen independently of one another from: methyl, ethyl, isopropyl, n-propyl, n-butyl, isobutyl, sec-butyl, tert-butyl, n-pentyl, n-hexyl, n-heptyl, n-octyl, cyclopropyl, cyclopentyl, cyclohexyl, phenyl, benzyl.

10. A synthesis agent according to claim 9, wherein the solvent contains tetrahydrofuran or 2-methyltetrahydrofuran.

11. A synthesis agent according to claim 9, wherein the diorganomagnesium compound is a dialkyl-, dialkenyl-, dialkynyl-, diaryl-, diheteroaryl -, alkylalkenyl-, alkylalkynyl-, alkylaryl-, alkylheteroaryl-, alkenylalkynyl-, alkenylaryl-, alkenylheteroaryl-, alkynylaryl- or alkynylheteroaryl-magnesium compound, preferably a di-n - alkyl-, di-sec-alkyl-, di-iso-alkyl-, di-tert-alkyl-, di-cycloalkyl-, di-aryl- and di-heteroaryl -magnesium compound, particularly preferably diethylmagnesium, di-isopropylmagnesium, di-n-propylmagnesium, di-n-butylmagnesium, di-sec-butylmagnesium, di-isobutylmagnesium, di-tert -butylmagnesium, di-cyclo-propylmagnesium, di-cyclopentyl-magnesium, di-cyclo-hexyl -magnesium, di-n-pentylmagnesium, di-n-hexylmagnesium, diphenylmagnesium, dibenzylmagnesium, n-butyl-n-octylmagnesium, n-butyl-ethylmagnesium, s-butyl -ethylmagnesium or s-butyl-n-butylmagnesium.

12. A process for the preparation of magnesium-containing synthesis agents and mixtures thereof with alkali-metal salts comprising reacting an alkali metal or an alloy thereof with a Grignard compound of formula RMgX and an organic of formula RX, wherein R is a saturated, unsaturated, branched, unbranched, functionalized, unfunctionalised, aliphatic, cyclic, heterocyclic or aromatic fragment, and
X is chlorine, bromine, iodine, tosylate or triflate.

13. A process according to claim 12, wherein magnesium is additionally added.

14. A process according to claim 12, wherein the alkali metal is lithium or a mixture or alloy containing lithium and another alkali metal, wherein the amount of lithium present is from 50 to 99.99 wt. %.

15. A process according to claim 12, wherein the molar ratio of the total amount of alkali metal to the total amount of compounds of the general formula RX is $2n/(n+m)$, the molar ratio of magnesium to the total amount of compounds of the general formula RX is $m/(n+m)$, and the molar ratio of the total amount of compound RMgX to the total amount of compound RX is $(p-m)/(n+m)$, wherein n is chosen between n 0.1 and 5 and m is between 0 and 53, and $(p-m) > 0$ wherein p is between 0 and 10.

16. A process according to claim 12, wherein n is between 0.8 and 1.8, m is between 0 and 1, and p is between 0 and 3.

17. A process according to claim 12, wherein for $n>m$.

18. A process according to claim 12, wherein $n>m$ and $p>n$.

19. A process according to claim 12, wherein a Grignard compound RMgX and an organic halide RX are used.

20. A process agent according to claim 12, wherein:
the lithium halides are chosen from the group lithium chloride, lithium bromide and lithium iodide;
the solvent is chosen from dimethyl ether, diethyl ether, dibutyl ether, methyl tert -butyl ether, cyclopentyl methyl ether, tetrahydrofuran, 2-methyltetrahydrofuran, toluene, cumene, xylenes, pentane, hexane, heptane, octane, cyclohexane and methylcyclohexane or any desired mixtures of at least two of these substances, and
R, is methyl, ethyl, isopropyl, n-propyl, n-butyl, isobutyl, sec-butyl, tert-butyl, n-pentyl, n-hexyl, n-heptyl, n-octyl, cyclopropyl, cyclopentyl, cyclohexyl, phenyl, benzyl.

21. A process according to claim 12, wherein the solvent contains tetrahydrofuran or 2-methyltetrahydrofuran.

* * * * *